United States Patent [19]

Ayers et al.

[11] Patent Number: 5,405,375
[45] Date of Patent: Apr. 11, 1995

US005405375A

[54] COMBINED MAPPING, PACING, AND DEFIBRILLATING CATHETER

[75] Inventors: Gregory M. Ayers, Duvall, Wash.; Joseph M. Smith, St. Louis, Mo.

[73] Assignee: InControl, Inc., Redmond, Wash.

[21] Appl. No.: 184,375

[22] Filed: Jan. 21, 1994

[51] Int. Cl.⁶ .............................................. A61N 1/05
[52] U.S. Cl. ................................... 607/122; 128/642; 607/37; 607/148
[58] Field of Search ................... 607/122, 37, 38, 148, 607/123, 124–128, 133; 128/642

[56] References Cited
U.S. PATENT DOCUMENTS

| 4,010,755 | 3/1977 | Preston | 607/122 |
| 4,355,646 | 10/1982 | Kallok et al. | 607/122 |
| 4,892,102 | 1/1990 | Astrinsky | 128/642 |
| 5,172,694 | 12/1992 | Flammang et al. | 607/122 |

Primary Examiner—William E. Kamm
Assistant Examiner—Kennedy J. Schaetzle
Attorney, Agent, or Firm—Richard O. Gray, Jr.

[57] ABSTRACT

A catheter insertable into a body provides for both sensing electrical activity of the heart at localized locations of the heart and defibrillating the heart when defibrillation is required. The catheter includes a plurality of connectors at the proximal end and a plurality of electrodes disposed along the catheter at the distal end. The plurality of electrodes includes a first plurality of electrodes and a second plurality of electrodes. The first plurality of electrodes are coupled together and to a given one of the plurality of connectors. Each of the second plurality of electrodes is coupled to a respective different one of the plurality of connectors. The first plurality of electrodes provide for defibrillating the heart and the second plurality of electrodes provide for sensing electrical activity of the heart at localized locations of the heart.

15 Claims, 1 Drawing Sheet

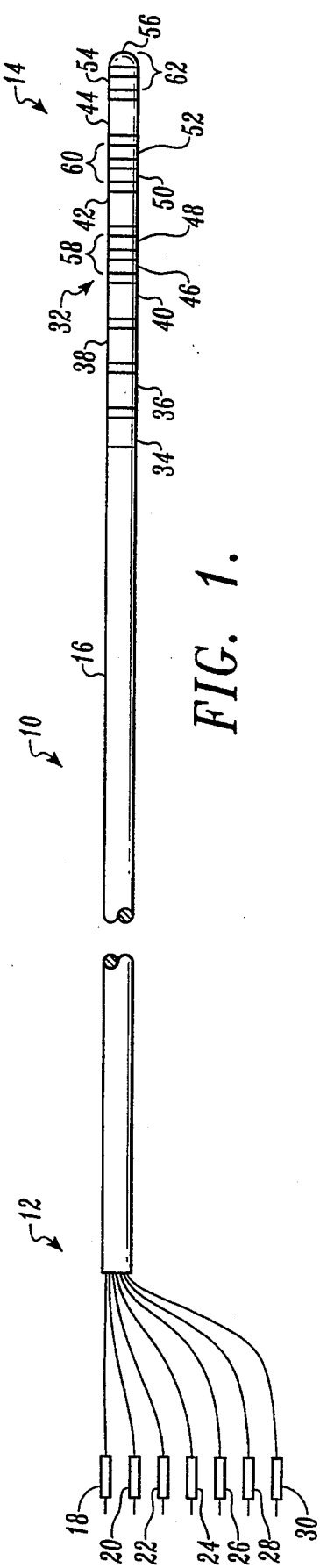
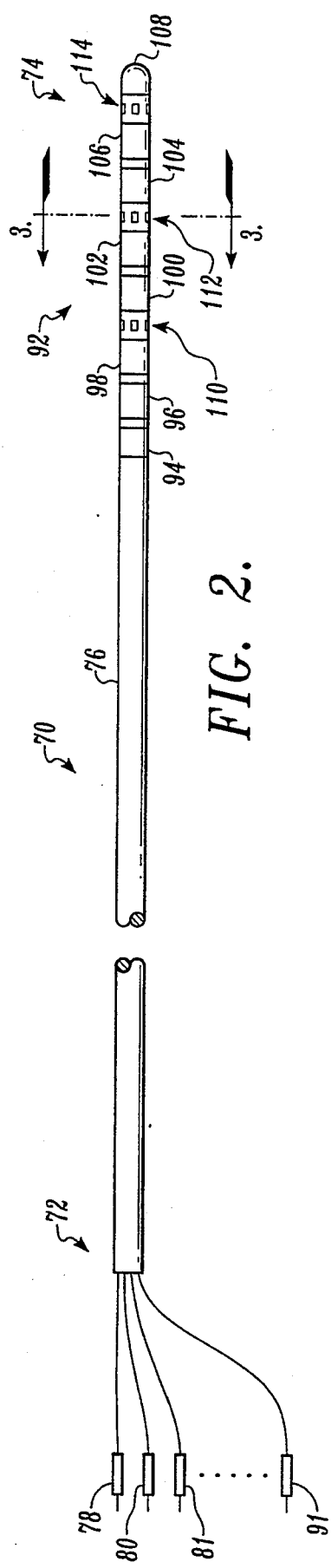
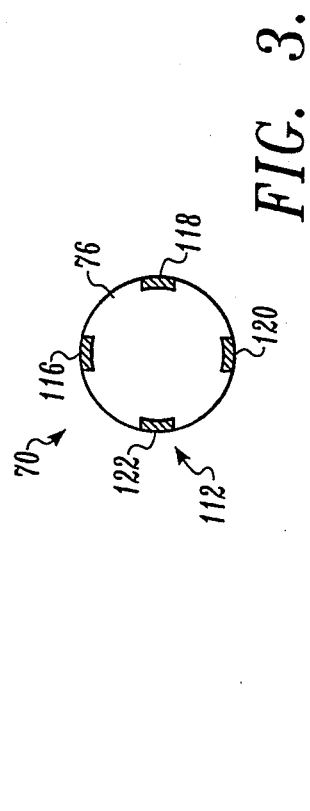

COMBINED MAPPING, PACING, AND DEFIBRILLATING CATHETER

BACKGROUND OF THE INVENTION

The present invention generally relates to mapping catheters for sensing electrical activity of the heart at localized locations of the heart. The present invention is more particularly directed to such a catheter which is capable of both sensing electrical activity of the heart at localized locations of the heart for mapping and for defibrillating the heart.

Mapping catheters or leads are well known in the art. Such leads include, at their distal ends, a plurality of closely spaced, relatively small surface area, electrodes. These electrodes may be disposed axially along the lead at the lead distal end or disposed in spaced apart and aligned relation about the lead at its distal end. Each electrode is coupled to a respective different connecter, referred to in the art as a tail, at the proximal end of the lead.

In use, the distal end of the lead is inserted through the skin of the patient into a vein or artery and then advanced so its distal end is within the heart or within a vein or artery associated with the heart. The connectors are then connected to external amplifier and display or recording equipment.

The lead is then manipulated or maneuvered into various positions. At each position, adjacent electrodes are utilized as electrode bipolar pairs to sense electrical activity of the heart. Because the electrodes are closely spaced, the electrodes sense electrical activity of the heart at localized locations and the resulting ECGs are displayed or recorded. The foregoing procedure is known as mapping and is utilized during electrophysiology studies.

During such studies, electrical energy may be applied to the electrode pairs to pace the heart. As a result of such applied electrical energy, fibrillation, such as atrial fibrillation, may accidentally be induced in the heart. Such fibrillation must be terminated by cardioversion before the mapping procedure can resume.

In order to cardiovert such fibrillation, in the prior art, it has been necessary to remove the mapping catheter and heavily sedate the patient. Once the patient is sedated, an external defibrillator with external pads is used to transthoracically cardiovert the heart. As is well known in the art, such external defibrillation requires high intensity energy.

Unfortunately, the need to externally defibrillate a patient undergoing a mapping procedure has many disadvantages. First, because some time may pass before the patient is sedated enough to be ready for external defibrillation, it can be more difficult to successfully cardiovert the heart. This may require higher defibrillation energies with the concomitant risk of causing large area skin burns on the patient.

Second, after successful cardioversion, patients may require thirty to sixty minutes of rest before the mapping procedure can resume. In some cases, patients are even required to rest overnight in the hospital before the mapping procedure can resume the next day. This obviously increases the time and inconvenience in completing a mapping procedure. Another disadvantage is that it is often difficult to replicate the last position of the mapping catheter when the mapping procedure is resumed. This lends to decreasing the accuracy of the mapping procedure results.

The present invention overcomes the aforementioned disadvantages of the prior art. To that end, the present invention provides a temporary mapping catheter capable of both sensing electrical activity of the heart at localized locations of the heart and defibrillating the heart when defibrillation is required. In accordance with one embodiment of the present invention, the mapping catheter may further be used for applying electrical energy to the heart for establishing pacing or defibrillation thresholds.

SUMMARY OF THE INVENTION

The present invention provides a catheter insertable into a body for both defibrillating a heart and sensing electrical activity of the heart at localized locations of the heart wherein the lead includes a proximal end and a distal end. The catheter comprises a plurality of connectors at the proximal end and a plurality of electrodes disposed along the catheter at the distal end. The plurality of electrodes includes a first plurality of electrodes and a second plurality of electrodes. The first plurality of electrodes are coupled together and to a given one of the plurality of connectors. Each electrode of the second plurality of electrodes is coupled to a respective different one of the plurality of connectors. The first plurality of electrodes provides for defibrillation of the heart and the second plurality of electrodes provides for the sensing of electrical activity of the heart at localized locations of the heart.

BRIEF DESCRIPTION OF THE DRAWINGS

The features of the present invention which are believed to be novel are set forth with particularity in the appended claims. The invention, together with further advantages thereof, may best be understood by making reference to the following description taken in conjunction with the accompanying drawing, in the several figures of which like reference numerals identify identical elements, and wherein:

FIG. 1 is a side plan view of a first catheter or lead embodying the present invention;

FIG. 2 is a side plan view of a second catheter or lead embodying the present invention; and FIG. 3 is a cross-sectional view taken along lines 3—3 of FIG. 2.

DESCRIPTION OF THE PREFERRED EMBODIMENTS

Referring now to FIG. 1, it illustrates in side plan view a first catheter or lead 10 embodying the present invention. The catheter 10 generally includes a proximal end 12, a distal end 14, and a generally cylindrical surface 16. The catheter 10 further includes a plurality of connectors 18, 20, 22, 24, 26, 28, and 30 at the proximal end 12. The catheter 10 further includes a plurality of ring-shaped electrodes 32 disposed along the distal end 14. The plurality of electrodes 32 include a first plurality of electrodes 34, 36, 38, 40, 42, and 44 and a second plurality of electrodes 46, 48, 50, 52, 54, and 56.

In accordance with this preferred embodiment, the first plurality of electrodes 34, 36, 38, 40, 42, and 44 are all coupled together. The first plurality of electrodes is also coupled to a given one of the plurality of connectors, such as to connector 18.

Each of the second plurality of electrodes 46, 48, 50, 52, 54, and 56 is coupled to a respective different one of connectors 20, 22, 24, 26, 28, and 30. To that end, electrode 46 may be coupled to connector 20, electrode 48 may be coupled to connector 22, electrode 50 may be coupled to connector 24, electrode 52 may be coupled to connector 26, electrode 54 may be coupled to connector 28, and electrode 56 may be coupled to connector 30. The connector 18 is adapted for being connected to an external defibrillating device and connectors 20, 22, 24, 26, 28, and 30 are adapted for connection to an external ECG display or chart recorder.

As will be noted in FIG. 1, each one of the first plurality of electrodes 34, 36, 38, 40, 42, and 44 has a surface area which is greater than the surface area of each of the second plurality of electrodes 46, 48, 50, 52, 54, and 56. More specifically, each of the first plurality of electrodes has a surface area which is greater than twice the surface area of each one of the second plurality of electrodes. Preferably, all of the electrodes have the same diameter dimension while each of the first plurality of electrodes has a length of five millimeters and each of the second plurality of electrodes has a length of one to three millimeters and preferably two millimeters. Also, adjacent electrodes are preferably spaced apart by an equal distance of, for example, one to two millimeters and preferably two millimeters.

As will be also noted in FIG. 1, the second plurality of electrodes are arranged in electrode pairs. To that end, electrodes 46 and 48 form a first electrode pair 58, electrodes 50 and 52 form a second electrode pair 60, and electrodes 54 and 56 form a third electrode pair 62. Selected ones of the first plurality of electrodes are disposed between the electrode pairs. To that end, electrode 42 is disposed between electrode pairs 58 and 60, and electrode 44 is disposed between electrode pairs 60 and 62. Further, electrodes 34, 36, 38, and 40 of the first plurality of electrodes are immediately adjacent to each other.

In use, the catheter is inserted through the skin and into a vein or artery of the patient and the catheter distal end is then advanced into the heart or into a vein or artery associated with the heart in a known manner. The electrode pairs 58, 60, and 62 are then utilized for sensing electrical activity of the heart at localized locations of the heart and/or for applying electrical energy to the heart for pacing the heart. If, during the use of the electrode pairs 58, 60, or 62 fibrillation, such as atrial fibrillation, is accidentally induced, the connector 18 is coupled to the external defibrillating device (not shown). Because the first plurality of electrodes are relatively large in surface area and coupled together, they collectively will serve as a first defibrillating electrode for cardioverting the heart. A second defibrillating electrode may be provided by a second temporary lead or by a large surface area chest wall electrode. Thereafter, cardioverting electrical energy is applied between the first plurality of electrodes 34, 36, 38, 40, 42, and 44 and the aforementioned second defibrillating electrode. As a result, the heart may be cardioverted without requiring the removal of the catheter or lead 10 from the heart.

Referring now to FIG. 2, it illustrates in side plan view another catheter or lead 70 embodying the present invention. The catheter 70 includes a proximal end 72, a distal end 74, and a generally cylindrical outer surface 76. The catheter 70 further includes a plurality of connectors 78 and 80–91 at the proximal end 72. The catheter 70 further includes a plurality of electrodes 92 at the distal end 74.

The plurality of electrodes 92 includes a first plurality of electrodes 94, 96, 98, 100, 102, 104, 106, and 108 and a second plurality of electrodes including electrode groups 110, 112, and 114. As may be best seen in FIG. 3, each of the electrode groups, such as electrode group 112 includes a plurality of electrodes 116, 118, 120, and 122 disposed in non-touching and aligned relation about the cylindrical surface 76 of the catheter 70. Preferably, each of the electrode groups includes four electrodes. As will be also noted in FIG. 3, the electrodes 116, 118, 120, and 122 are equally spaced about the cylindrical surface 76 so that electrodes 118 and 122 are orthogonally disposed with respect to electrodes 116 and 120.

As will be further noted in FIG. 2, selected pairs of the first plurality of electrodes are disposed on opposite sides of the electrode groups 110, 112, and 114. More specifically, electrodes 98 and 100 are disposed on opposite sides of electrode group 110, electrodes 102 and 104 are disposed on opposite sides of electrode group 112, and electrodes 106 and 108 are disposed on opposite sides of electrode group 114.

As in the first embodiment of FIG. 1, all of the first plurality of electrodes 94, 96, 98, 100, 102, 104, 106, and 108 are coupled together and to the connector 78. Each of the second plurality of electrodes, as in the embodiment of FIG. 1, is coupled to a respective different one of the connectors 80–91.

In use of the mapping catheter or lead 70, the second plurality of electrodes may be utilized for sensing electrical activity of the heart at localized locations of the heart. Should, during the mapping procedure, fibrillation, such as atrial fibrillation of the heart occur, the connector 78 may be coupled to an external defibrillating device (not shown) to permit cardioverting electrical energy to be applied to the first plurality of electrodes 94, 96, 98, 100, 102, 104, 106, and 108. Because the surface area of each of the first plurality of electrodes is relatively large, and because the first plurality of electrodes are all coupled together, they serve as a first cardioverting electrode for cardioverting the heart. In accordance with this preferred embodiment, each of the first plurality of electrodes is five millimeters in length and each of the second plurality of electrodes is one millimeter by one millimeter in dimension. In addition, the electrodes and electrode groups are spaced apart by an equal distance of, for example, two millimeters.

By virtue of the present invention, a temporary catheter or lead has been provided which is capable of sensing electrical activity of the heart at localized locations thereof for mapping and cardioverting the heart. In accordance with the embodiment of FIG. 1, the catheter or lead 10 may also be utilized for applying electrical energy to the heart through the second plurality of electrodes to pace the heart.

Hence, should fibrillation, such as atrial fibrillation, occur during the mapping procedure, by virtue of the first plurality of electrodes being of relatively large surface area and coupled together to serve as a first cardioverting electrode, the catheters or leads of the present invention need not be explanted to permit cardioversion of the heart. More importantly, the temporary catheters of the present invention negate the need for external defibrillation. Because the catheter is within or closely adjacent to the heart, much lower cardioverting energies are required. This avoids the risk of burning the patient and even renders sedation unnecessary. Further, after successful cardioversion, the mapping procedure can immediately resume. As a result, the time for completing a mapping procedure is not unduly extended. This makes such a mapping procedure more convenient and reduces the discomfort to the patient undergoing the electrophysiology study.

While particular embodiments of the present invention have been shown and described, modifications may be made, and it is therefore intended in the appended claims to cover all such changes and modifications which fall within the true spirit and scope of the invention.

What is claimed is:

1. A catheter insertable into a body for both defibrillating a heart and sensing electrical activity of the heart at localized locations of the heart, said catheter including a proximal end and a distal end and comprising:
   a plurality of connectors at said proximal end; and
   a plurality of electrodes disposed along said catheter at said distal end, said plurality of electrodes including a first plurality of electrodes and a second plurality of electrodes, said first plurality of electrodes being coupled together to a given one of said plurality of connectors, each said electrode of said second plurality of electrodes being coupled to a respective different one of said plurality of connectors, said first plurality of electrodes for defibrillating the heart, and said second plurality of electrodes for sensing electrical activity of the heart at localized locations of the heart, wherein each one of said first plurality of electrodes has a surface area, wherein each one of said second plurality of electrodes has a surface area, and wherein the surface area of at least one of said first plurality of electrodes is greater than twice the surface area of at least one of said second plurality of electrodes.

2. A catheter as defined in claim 1 wherein said lead has a generally cylindrical surface and wherein said second plurality of electrodes includes at least one electrode group including a plurality of discrete electrodes disposed in non-touching relation circumferentially about said cylindrical surface.

3. A catheter as defined in claim 2 wherein said discrete electrodes of said electrode group are in axially aligned relation about said cylindrical surface.

4. A catheter as defined in claim 1 wherein said at least one of said second plurality of electrodes is more distal on said catheter than any other of said electrodes.

5. A catheter as defined in claim 1 wherein the electrodes of said first plurality of electrodes are interspersed with the electrodes of said second plurality of electrodes along said catheter.

6. A catheter insertable into a body for both defibrillating a heart and sensing electrical activity of the heart at localized locations of the heart, said catheter including a proximal end and a distal end and comprising:
   a plurality of connectors at said proximal end; and
   a plurality of electrodes disposed along said catheter at said distal end, said plurality of electrodes including a first plurality of electrodes and a second plurality of electrodes, said first plurality of electrodes being coupled together to a given one of said plurality of connectors, each said electrode of said second plurality of electrodes being coupled to a respective different one of said plurality of connectors, said first plurality of electrodes for defibrillating the heart, and said second plurality of electrodes for sensing electrical activity of the heart at localized locations of the heart, wherein each one of said first plurality of electrodes has a surface area, wherein each one of said second plurality of electrodes has a surface area, and wherein the surface area of each one of said first plurality of electrodes is greater than twice the surface area of each one of said second plurality of electrodes.

7. A catheter as defined in claim 6 wherein said second plurality of electrodes includes at least one electrode pair including two immediately adjacent electrodes.

8. A catheter as defined in claim 7 wherein said second plurality of electrodes includes a plurality of said electrode pairs.

9. A catheter as defined in claim 8 wherein selected ones of said first plurality of electrodes are disposed between said electrode pairs.

10. A catheter as defined in claim 9 wherein a plurality of said first plurality of electrodes are immediately adjacent to each other.

11. A catheter insertable into a body for both defibrillating a heart and sensing electrical activity of the heart at localized locations of the heart, said catheter including a proximal end and a distal end and comprising:
    a plurality of connectors at said proximal end; and
    a plurality of electrodes disposed along said catheter at said distal end, said plurality of electrodes including a first plurality of electrodes and a second plurality of electrodes, said first plurality of electrodes being coupled together to a given one of said plurality of connectors, each said electrode of said second plurality of electrodes being coupled to a respective different one of said plurality of connectors, said first plurality of electrodes for defibrillating the heart, and said second plurality of electrodes for sensing electrical activity of the heart at localized locations of the heart,
    wherein said lead has a generally cylindrical surface and wherein said second plurality of electrodes includes at least one electrode group including a plurality of electrodes disposed in aligned non-touching relation about said cylindrical surface, and
    wherein said second plurality of electrodes include a plurality of said electrode groups.

12. A catheter as defined in claim 11 wherein each said electrode group includes four electrodes.

13. A catheter as defined in claim 12 wherein said four electrodes of each said electrode group are equally spaced about said cylindrical surface.

14. A catheter as defined in claim 11 wherein selected pairs of said first plurality of electrodes are disposed on opposite sides of said electrode groups.

15. A catheter as defined in claim 14 wherein a plurality of said first plurality of electrodes are immediately adjacent to each other.

* * * * *